(12) United States Patent
Niddam-Hildesheim et al.

(10) Patent No.: US 7,531,656 B2
(45) Date of Patent: May 12, 2009

(54) SYNTHESIS OF GATIFLOXACIN

(75) Inventors: Valerie Niddam-Hildesheim, Ein Vered (IL); Ben-Zion Dolitzky, Petach Tiqva (IL); Gideon Pilarski, Holon (IL); Greta Sterimbaum, Rishon-Lezion (IL)

(73) Assignee: Teva Pharmaceuticals USA, Inc., North Wales, PA (US)

( * ) Notice: Subject to any disclaimer, the term of this patent is extended or adjusted under 35 U.S.C. 154(b) by 1004 days.

(21) Appl. No.: 10/641,750

(22) Filed: Aug. 14, 2003

(65) Prior Publication Data

US 2005/0080264 A1    Apr. 14, 2005

Related U.S. Application Data

(60) Provisional application No. 60/403,514, filed on Aug. 14, 2002, provisional application No. 60/461,202, filed on Apr. 7, 2003.

(51) Int. Cl.
*C07D 211/06* (2006.01)
*C07D 403/04* (2006.01)
*C07D 401/04* (2006.01)

(52) U.S. Cl. ............... 544/363; 546/156; 546/184; 546/195

(58) Field of Classification Search ......... 546/152, 546/156, 185, 195, 155; 544/363
See application file for complete search history.

(56) References Cited

U.S. PATENT DOCUMENTS

| 4,980,470 A | 12/1990 | Masuzawa et al. |
| 4,997,943 A | 3/1991 | Iwata et al. |
| 5,051,505 A | 9/1991 | Park et al. |
| 5,053,407 A | 10/1991 | Hayakawa et al. |
| 5,155,223 A | 10/1992 | Preiss |
| 5,157,117 A | 10/1992 | Takagi et al. |
| 5,539,110 A | 7/1996 | Kim et al. |
| 5,880,283 A | 3/1999 | Matsumoto et al. |

FOREIGN PATENT DOCUMENTS

| EP | 0 230 295 | 7/1987 |
| WO | WO 02/22126 A1 | 3/2002 |

OTHER PUBLICATIONS

Keun-Soo Nam et al., "A New Efficient Coupling Agent in the Synthesis of Quinolone Antimicrobial Agents: Aluminum Oxide (Al2O3) and Resin," Korean Journal of Medicinal Chemistry, vol. 6, No. 2, pp. 157-161, 1996.

*Primary Examiner*—James O. Wilson
*Assistant Examiner*—Paul V. Ward
(74) *Attorney, Agent, or Firm*—Kenyon & Kenyon, LLP.

(57) ABSTRACT

Provided are a method for making (±)-1-Cyclopropyl-6-fluoro-1,4-dihydro-8-methoxy-7-(3-methyl-1-piperazinyl)-4-oxo-3-quinolenecarboxylic acid, commonly known as gatifloxacin, in high purity, in a suspension in a dipolar aprotic solvent.

15 Claims, No Drawings

SYNTHESIS OF GATIFLOXACIN

RELATED APPLICATIONS

The present application claims the benefit of the filing date of U.S. Provisional Patent Applications 60/403,514 filed on Aug. 14, 2002 and 60/461,202 filed on Apr. 7, 2003.

FIELD OF THE INVENTION

The present invention relates to the synthesis and purification of (±)-1-Cyclopropyl-6-fluoro-1,4-dihydro-8-methoxy-7-(3-methyl-1-piperazinyl)-4-oxo-3-quinolenecarboxylic acid, commonly known as gatifloxacin.

BACKGROUND OF THE INVENTION (±)-1-Cyclopropyl-6-fluoro-1,4-dihydro-8-methoxy-7-(3-methyl-1-piperazinyl)-4-oxo-3-quinolenecarboxylic acid, commonly known as gatifloxacin, is a synthetic broad-spectrum antibacterial agent for oral or intravenous administration.

U.S. Pat. No. 4,980,470 (cf European Patent 230,295), discloses the synthesis of gatifloxacin via the substitution of 2-methyl piperazine on the 9,10-difluoro carboxylic derivative. The reaction is described to occur in the absence of solvent or in the presence of organic polar solvent such as DMSO, pyridine, dimethylformamide, alcohol, water or hexamethylphosphoric amide (See '470 patent paragraph 3, line 52). This reaction can reportedly be carried-out in the presence of an acid acceptor such as triethylamine, diazabicyclo bases, or potassium carbonate. According to example 3 of the '407 patent, the yield of this reaction in DMSO is 20%.

The reaction conditions under which gatifloxacin is synthesized are reported to effect the yield and purity of the products obtained. Some common impurities in gatifloxacin include the following:

Desmethyl gatifloxacin (DesMe-GTF), 1-cyclopropyl-6-fluoro-1,4-dihydro-8-methoxy-7-(piperazinyl)-4-oxo-3-quinolenecarboxylic acid, is an impurity in gatifloaxacin:

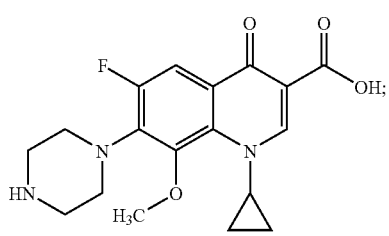

hydroxy gatifloxacin (OH-GTF), 1-cyclopropyl-6-fluoro-1,4-dihydro-8-hydroxy-7-(3-methyl-1-piperazinyl)-4-oxo-3-quinolinecarboxylic acid:

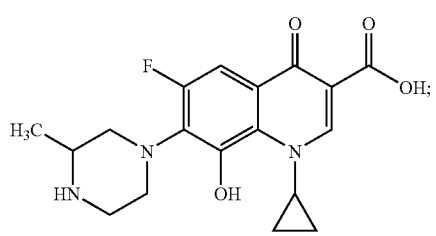

dimethyl gatifloxacin (DiMe-GTF), 1-cyclopropyl-6-fluoro-1,4-dihydro-8-hydroxy-7-(3,4-dimethyl-1-piperazinyl)-4-oxo-3-quinolinecarboxylic acid:

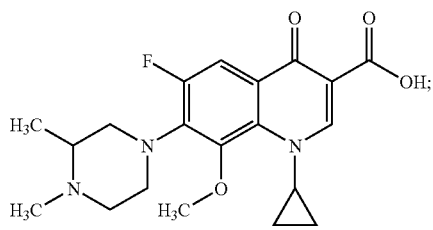

anti-gatifloxacin (Anti-GTF), 1-cyclopropyl-7-fluoro-1,4-dihydro-8-hydroxy-6-(3-methyl-1-piperazinyl)-4-oxo-3-quinolinecarboxylic acid:

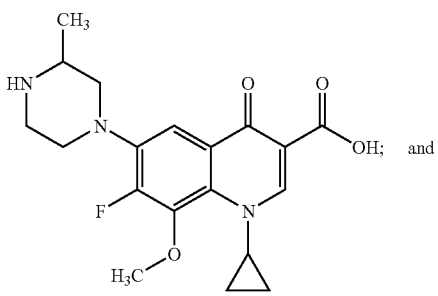

and 2-methyl piperazine gatifloxacin (2-Me-GTF), 1-cyclopropyl-6-fluoro-1,4-dihydro-8-methoxy-7-(2-methyl-1-piperazinyl)-4-oxo-3-quinolinecarboxylic acid:

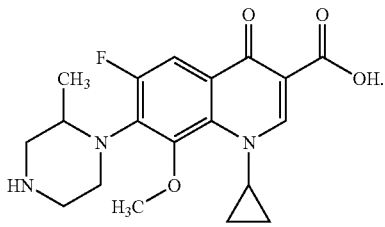

In Korean Journal of Medicinal Chemistry 1996, Vol.6, No 2,157-161 the nucleophilic substitution on GTF-acid is described in the presence of basic aluminium oxide or basic ion-exchange resins. The authors reported that they produced gatifloxacin with a yield above 85%. The present inventors reproduced several times these experiments in the same experimental conditions or modified conditions using the same catalysts and were only able to achieve yields of about 50%.

In U.S. Pat. No. 4,997,943 to Sankyo, the authors described the synthesis of gatifloxacin hydrochloride (See example 22 thereof) via a borate intermediate that activates the position 7 of the ring that will be substituted by the 2-methylpiperazine. This boron chelate allowed the authors to run the reaction at ambient temperature and to get a yield of 38%.

In U.S. Pat. No. 5,157,117, Kyorin described the synthesis of another borate intermediate suitable for industrial process.

This chelate should allow the authors to produce gatifloxacin in milder experimental conditions and reportedly in an overall yield of 76%.

The synthesis of levofloxacin is the same type of synthesis, i.e. a nucleophilic substitution of N-methylpiperazine (instead of 2-methylpiperazine) in position 7 of a quinolone.

In U.S. Pat. No. 5,053,407, directed to levofloxacin, the same reaction conditions as for gatifloxacin has been also described to provide 51% yield (example 6). In example 16 of the '407 patent, the same substitution is done through of a boron chelate to obtain 65% of levofloxacin.

U.S. Pat. Nos. 5,051,505 and 5,539,110 described the synthesis of levofloxacin in presence of phase transfer catalyst in order to allow less drastic reaction conditions. U.S. Pat. No. 5,155,223 describes the synthesis of levofloxacin in presence of water.

There is a need for a single-step synthetic route to gatifloxacin that allows manufacture of the product in good yield under mild conditions and in high purity.

SUMMARY OF THE INVENTION

In one aspect, the present invention relates to a method of making gatifloxacin including the steps of: heating a reaction mixture including 2-methylpiperazine and 1-cyclopropyl-6,7-difluoro-1,4-dihydro-8-methoxy-4-oxo-3-quinoline carboxylic acid in a dipolar aprotic solvent, especially DMSO, to a reaction temperature between about 40° C. and about 70° C. for a reaction time in an atmosphere of inert gas, especially nitrogen or argon; maintaining, especially with agitation, the reaction mixture at a holding temperature of about 40° C. or less for a holding time sufficiently long so that there is no further increase in percent suspended solids for a period of about one-half hour; and isolating gatifloxacin from the slurry thereby obtained. The reaction mixture can be made by combining, in several portions (i.e. portionwise) 1-cyclopropyl-6,7-difluoro-1,4-dihydro-8-methoxy-4-oxo-3-quinoline carboxylic acid with a mixture of dipolar aprotic solvent, especially DMSO, and 2-methylpiperazine.

In another aspect, the present invention relates to a method of making gatifloxacin including the steps of: heating a reaction mixture comprising 2-methylpiperazine and 1-cyclopropyl-6,7-difluoro-1,4-dihydro-8-methoxy-4-oxo-3-quinoline carboxylic acid in a dipolar aprotic solvent, especially DMSO, to a reaction temperature between about 40° C. and about 70° C., especially about 55° C., for a reaction time in an atmosphere of inert gas, especially nitrogen or argon; combining the reaction mixture with a cosolvent selected from benzene, toluene, dimethylcarbonate, and water; maintaining, especially with agitation, the combination of reaction mixture and cosolvent at a holding temperature of about 40° C. or less, especially about 25° C. or less, for a holding time sufficiently long so that there is no further increase in percent suspended solids for a period of about one-half hour; and isolating gatifloxacin from the slurry thereby obtained.

In yet another aspect, the present invention relates to a method of making gatifloxacin having about 0.07 area-% or less desmethyl gatifloxacin and about 0.06 area- % or less 2'-methylgatifloxacin including the steps of: heating a reaction mixture comprising 2-methylpiperazine and 1-cyclopropyl-6,7-difluoro-1,4-dihydro-8-methoxy-4-oxo-3-quinoline carboxylic acid in a dipolar aprotic solvent, especially DMSO, to a reaction temperature between about 40° C. and about 70° C., especially about 53° C. to about 57° C., for a reaction time in an atmosphere of inert gas, especially nitrogen or argon; optionally combining with the reaction mixture a cosolvent selected from benzene, toluene, dimethylcarbonate and water; maintaining, especially with agitation, the reaction mixture, whether or not concentrated and/or combined with cosolvent, at a holding temperature of about 40° C. or less, especially about 25° C. or less, most especially 5° C. or less, for a holding time sufficiently long so that there is no further increase in percent suspended solids for a period of about one-half hour; isolating gatifloxacin from the slurry thereby obtained; slurrying the isolated gatifloxacin with water or a mixture of acetonitrile and water; and isolating gatifloxacin having about 0.07 area-% or less desmethyl gatifloxacin and about 0.06 area-% or less 2'-methylgatifloxacin from the water slurry.

In another aspect, the present invention relates to gatifloxacin having about 0.1 area-% or less total impurities, in particular having less than about 0.06 area-% 2'-methyl gatifloxacin.

In yet a further aspect, the present invention relates to a pharmaceutical composition containing gatifloxacin made by any embodiments of the method of the present invention.

DETAILED DESCRIPTION OF THE INVENTION

As used herein, the term ambient temperature refers to a temperature of about 22° C. to about 28° C.

The present invention provides a method of making 1-cyclopropyl-6-fluoro-1,4-dihydro-8-methoxy-7-methyl-1-piperazinyl-4-oxo-3-quinolinecartboxylic acid, commonly known as gatifloxacin (I), from 1-cyclopropyl-6,7-difluoro-1,4-dihydro-8-methoxy-4-oxo-3-quinoline carboxylic acid (II) and 2-methylpiperaxine (III).

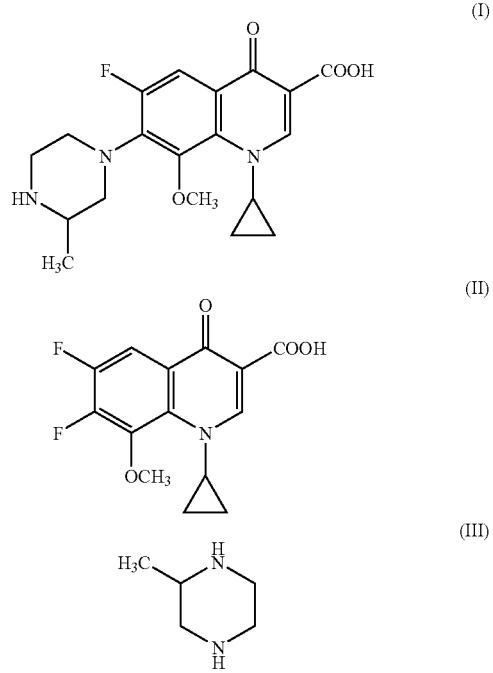

In a first step of the method of the present invention, 2-methylpiperazine III and II are mixed in a dipolar aprotic solvent in an inert atmosphere, substantially in the absence of oxygen, to provide a reaction mixture. Dipolar aprotic solvents useful in the practice of the present invention include N,N-dimethylformamide (DMF), N,N-dimethylacetamide (DMAC), N-methylpyrolidone (NMP), and dimethylsulfoxide (DMSO). Dimethylsulfoxide is the preferred dipolar aprotic solvent. The inert atmosphere can be any inert or noble gas. Nitrogen and argon are the preferred gases for the inert atmosphere. The suspension is heated to a reaction temperature above about 40° C. but not more than about 70° C. When DMSO is the dipolar aprotic solvent, the preferred reaction temperature is about 55° C.

The reaction mixture is maintained at the reaction temperature for a reaction time sufficient to effect reaction, typically at least about 12 hours. The skilled artisan will know to adjust the reaction time by monitoring the reaction by known techniques, for example chromatography. The resulting mixture includes the desired product, gatifloxacin. Optionally, the resulting mixture can then be concentrated to about 75% to about 33%, preferably about 50% of its initial volume. When used, the concentrating is most easily effected at reduced pressure, especially when DMSO is the dipolar aprotic solvent.

In a preferred embodiment, the reaction mixture is provided by combining II in several portions (i.e. portionwise) with a mixture of III and dipolar aprotic solvent. In this way, the amount of dipolar aprotic solvent used can be minimized, making the optional concentration step superfluous.

In a subsequent step of the method of the present invention, the optionally concentrated mixture is held, and preferably agitated, at a holding temperature less than about 40° C., preferably less than about 30° C., most preferably less than about 25° C. The temperature of the holding step is limited by the viscosity or solidification of the solvent. If desired, a cosolvent can be added to the optionally concentrated reaction mixture to reduce the viscosity or to inhibit solidification, and to increase the amount of product that ultimately precipitates. When a cosolvent is used, the combination of optionally concentrated mixture and cosolvent can be held at a lower temperatures whilst still remaining stirrable.

A cosolvent is a solvent that is miscible with the polar aprotic solvent. Preferred cosolvents include water, dimethyl carbonate, benzene, and toluene.

During the holding time, gatifloxacin crystallizes from the mixture. The holding is continued for a holding time, typically between about 12 to 18 hours. The time of the holding step can be determined by routine optimization by monitoring, for example, the percent solids in the slurry obtained. Percent solids indicates that portion, by weight, of the slurry that is comprised of solids. Percent solids can be determined by a variety of means known to the skilled artisan. The slurry can be maintained at the holding temperature until the percent solids remains essentially constant over any one-half hour interval of the maintaining (holding) step (i.e. the increase over the interval is less than about 1 percent).

The product can be isolated in hitherto unachieved yields, with low content of dealkylation product, by separating the solids from the slurry by any means known in the art, for example filtration (gravity or suction) or centrifugation, to mention just two. The product obtained is substantially free of impurities.

In a preferred embodiment of the present invention, DMSO is the dipolar aprotic solvent. In this embodiment, the method of the present invention includes the step, prior to the holding step, of concentrating the slurry containing produced gatifloxacin, preferably by distilling-off a portion, typically ⅓ to ¾ of the dipolar aprotic solvent. The dipolar aprotic solvent is preferably distilled-off at reduced pressure, preferably at a pressure less than about 10 mm Hg, most preferably less than about 5 mm Hg and a temperature of about 70° C. or less. The slurry is concentrated until the volume of the slurry is reduced to at least about half of the original volume. The slurry can be concentrated to dryness. As discussed above, the concentrating step can be rendered superfluous if the reaction mixture is provided by combining 1-cyclopropyl-6,7-difluoro-1,4-dihydro-8-methoxy-4-oxo-3-quinoline carboxylic acid (II) with a mixture of dipolar aprotic solvent and 2-methylpiperazine (III).

In a particularly preferred embodiment, the method of the present invention includes the step of slurrying the gatifloxacin, isolated after the holding time, in water or a mixture of water and acetonitrile at about 20° C. to about 30° C. This embodiment is particularly useful when the gatifloxacin to be slurried is made using DMSO solvent at a reaction temperature of about 53° C. to about 57° C. The slurrying is carried-out for a slurry time of about 30 minutes to about 3 hours. The amount of water used to slurry the gatifloxacin will typically be about 4 mL to about 10 mL per gram of gatifloxacin to be slurried.

After the slurry time, the slurried gatifloxacin can be isolated by any means known in the art, for example filtration (gravity or suction) or centrifugation, to mention just two.

Gatifloxacin prepared according to this particularly preferred embodiment has a low level of impurities as determined by HPLC. For example, it contains about 0.07 are- % or less desmethyl gatifloxacin and 0.06 area- % or less 2'-methyl gatifloxacin. Area percent refers to the relative area under the corresponding peak in the HPLC chromatogram that can be obtained as described below.

HPLC analysis can be performed at 38° C. on a J'spher H-80 column (4.6×150 mm, 4 μm, 8 mm) using a gradient eluent of first eluent A and second eluent B. Eluent A includes 86% buffer and 14% acetonitrile. Eluent B includes 50% buffer, 40% acetonitrile, and 10% methanol. The buffer includes 0.04M ammonium acetate and 0.06M sodium perchlorate monohydrate, adjusted to pH 2.2 with $H_3PO_4$. A UV detector at 285 nm is used. The injection volume is 20 μL. Samples (ca. 20 mg) are dissolved in 10% acetonitrile in water (ca. 50 mL).

The gradient is as follows:

| | | Eluent Program: | | |
|---|---|---|---|---|
| Line | Time | Flow | Eluent A | Eluent B |
| 1 | 0 | 2.0 | 95 | 5 |
| 2 | 15 | 2.0 | 95 | 5 |
| 3 | 28 | 2.0 | 20 | 80 |
| 4 | 35 | 2.0 | 20 | 80 |

In yet another embodiment, the present invention provides pharmaceutical compositions including the gatifloxacin having a low level of impurities made by the method of the present invention, The pharmaceutical composition can be in the form of a solid oral dosage form (e.g., compressed tablets or capsules), or it can be in the form of a liquid oral dosage form (e.g., a solution or oral suspension).

Compressed tablets can be made by dry or wet granulation methods as is known in the art. In addition to the pharmaceutically active agent or drug, compressed tablets contain a number of pharmacologically inert ingredients, referred to as excipients. Some excipients allow or facilitate the processing of the drug into tablet dosage forms. Other excipients contribute to proper delivery of the drug by, for example, facilitating disintegration.

Excipients can be broadly classified according to their intended function. This classification is sometimes arbitrary and it is known that a particular excipient can function in more than one way or serve more than one purpose in a formulation.

Diluents increase the bulk of a solid pharmaceutical composition and may make a pharmaceutical dosage form containing the composition easier for the patient and caregiver to handle. Diluents for solid compositions include, for example, microcrystalline cellulose (e.g., AVICEL®, microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium alginate and starch. The dissolution rate of a compacted solid pharmaceutical composition in the patient's stomach may be increased by the addition of a disintegrant to the composition.

Disintegrants include alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®) and starch.

Glidants can be added to improve the flow properties of non-compacted solid compositions and improve the accuracy of dosing. Excipients that may function as glidants include colloidal silicon dioxide, magnesium trisilicate, powdered cellulose, starch, talc and tribasic calcium phosphate.

When a dosage form such as a tablet is made by compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease release of the product from the die. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid ethyl maltol, and tartaric acid.

Solid and liquid compositions may also be colored using any pharmaceutically acceptable colorant to improve their appearance and/or facilitate patient identification of the product and unit dosage level.

Of course, wet or dry granulate can also be used to fill capsules, for example gelatin capsules. The excipients chosen for granulation when a capsule is the intended dosage form may or may not be the same as those used when a compressed tablet dosage form is contemplated.

Selection of excipients and the amounts to use may be readily determined by the formulation scientist based upon experience and consideration of standard procedures and reference works in the field.

In liquid pharmaceutical compositions of the present invention, gatifloxacin having a low level of impurities made by the method of the present invention and any solid excipients are dissolved or suspended in a liquid carrier such as water, vegetable oil, alcohol, polyethylene glycol, propylene glycol or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention can also contain a viscosity enhancing agent to improve the mouth-feel of the product and/or coat the lining of the gastrointestinal tract. Such agents include, for example, acacia, alginic acid, bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste.

Preservatives and chelating agents such as alcohol, sodium benzoate, butylated hydroxy toluene, butylated hydroxyanisole and ethylenediamine tetraacetic acid can be added at levels safe for ingestion to improve storage stability.

A liquid composition according to the present invention can also contain a buffer such as gluconic acid, lactic acid, citric acid or acetic acid, sodium gluconate, sodium lactate, sodium citrate or sodium acetate.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. The most suitable route in any given case will depend on the nature and severity of the condition being treated. The dosages can be conveniently presented in unit dosage form and prepared by any of the methods well-known in the pharmaceutical arts.

Dosage forms include solid dosage forms like tablets, powders, capsules, suppositories, sachets, troches and losenges as well as liquid syrups, suspensions and elixirs.

The active ingredient and excipients can be formulated into compositions and dosage forms according to methods known in the art.

A composition for tableting or capsule filling can be prepared by wet granulation. In wet granulation some or all of the active ingredients and excipients in powder form are blended and then further mixed in the presence of a liquid, typically water, which causes the powders to clump up into granules. The granulate is screened and/or milled, dried and then screened and/or milled to the desired particle size. The granulate can then be tableted or other excipients can be added prior to tableting, such as a glidant and/or a lubricant.

A tableting composition can be prepared conventionally by dry blending. For instance, the blended composition of the active ingredients and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules. Excipients that are particularly well-suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, only they are not subjected to a final tableting step.

Capsules, tablets and lozenges and other unit dosage forms may be administered in various dosages depending on the need.

The present invention can be further illustrated by the following non-limiting examples.

EXAMPLE 1

Ninety grams of 1-cyclopropyl-6,7-difluoro-1,4-dihydro-8-methoxy-4-oxo-3-quinoline carboxylic acid and 64 g (2.1 eq) of 2-methyl piperazine were put in suspension in 1.8 liter of DMSO under nitrogen atmosphere. The mixture was heated to 55° C. during 24 hours. Subsequently, the mixture was heated to 70° C. and half of the amount of DMSO was distilled-off at reduced pressure (1-5 mm Hg). At the end of the distillation, the reaction mixture was cooled to 20° C. and left at this temperature overnight. The solution was then filtered under vacuum and the wet cake washed twice with n-butanol (300 ml). The collected solid was then dried under vacuum to obtain 94 g. The calculated yield, after assay, was 84%.

EXAMPLE 2

Twenty grams of 1-cyclopropyl-6,7-difluoro-1,4-dihydro-8-methoxy-4-oxo-3-quinoline carboxylic acid and 14.2 g (2.1 eq) of 2-methyl piperazine were suspended in DMSO (400 mL) under a blanket of nitrogen. The mixture was heated to 55° C. during 24 hours. Subsequently, the mixture was heated to 70° C. and half of the amount of DMSO was distilled-off at reduced pressure (1-5 mm Hg). At the end of the distillation, dimethylcarbonate (200 mL) was added, the reaction mixture was cooled to 5° C. and held at this temperature overnight. The mixture was then filtered under vacuum. The compound was then dried under vacuum to obtain 20.22 g after assay (76% yield) of gatifloxacin.

EXAMPLE 3

Forty grams of 1-cyclopropyl-6,7-difluoro-1,4-dihydro-8-methoxy-4-oxo-3-quinoline carboxylic acid and 28.4 g (2.1 eq) of 2-methyl piperazine were suspended in DMSO (800 mL) under nitrogen atmosphere. The mixture was heated to 55° C. during 24 hours. Thereafter, dimethylcarbonate (200 mL) was added, the reaction mixture was cooled to 5° C., and held at this temperature overnight. The mixture was then filtered under vacuum and the compound was then dried under vacuum to obtain 35.5 g after assay (70% yield) of gatifloxacin.

EXAMPLE 4

Forty grams of 1-cyclopropyl-6,7-difluoro-1,4-dihydro-8-methoxy-4-oxo-3-quinoline carboxylic acid and 28.4 g (2.1 eq) of 2-methyl piperazine were put in suspension in DMSO (800 mL) under nitrogen atmosphere. The mixture was heated to 55° C. during 24 hours. Subsequently, the mixture was heated to 70° C. and half of the amount of DMSO was distilled-off at reduced pressure (1-5 mm Hg). At the end of the distillation, toluene (200 mL) was added, the reaction mixture was cooled to 5° C., and held at this temperature overnight. The solution was filtered and dried under vacuum to obtain 38 g after assay (75% yield) of gatifloxacin.

EXAMPLE 5

Forty grams of 1-cyclopropyl-6,7-difluoro-1,4-dihydro-8-methoxy-4-oxo-3-quinoline carboxylic acid and 28.4 g (2.1 eq) of 2-methyl piperazine were put in suspension in DMSO (800 mL) under nitrogen blanket. The mixture was heated to 55° C. during 24 hours. Subsequently, toluene (200 mL) was added, the reaction mixture was cooled to 5° C., and held at this temperature overnight. The solution was filtered and dried under vacuum to obtain 43.5 g after assay (76% yield) of gatifloxacin.

EXAMPLE 6

Thirty five grams of 1-cyclopropyl-6,7-difluoro-1,4-dihydro-8-methoxy-4-oxo-3-quinoline carboxylic acid and 24.9 g (2.1 eq) of 2-methyl piperazine were put in suspension in DMSO (700 mL) under nitrogen atmosphere. The mixture was heated to 55° C. during 24 hours. The reaction mixture was then stirred at 20° C. overnight. Half of this solution (408 g, assay 4.8%) was filtrated and dried under vacuum to obtain 15.0 g (66% yield) of gatifloxacin.

EXAMPLE 7

Thirty five grams of 1-cyclopropyl-6,7-difluoro-1,4-dihydro-8-methoxy-4-oxo-3-quinoline carboxylic acid and 24.9 g (2.1 eq) of 2-methyl piperazine were put in suspension in DMSO (700 mL) under nitrogen atmosphere. The mixture was heated to 55° C. during 24 hours.

One hundred fifteen grams (assay 4.81%) of this solution were distilled to dryness and 40 ml of toluene were added to give 5.82 g after assay (82.7% yield) of gatifloxacin.

EXAMPLE 8

Thirty five grams of 1-cyclopropyl-6,7-difluoro-1,4-dihydro-8-methoxy-4-oxo-3-quinoline carboxylic acid and 24.9 g (2.1 eq) of 2-methyl piperazine were suspended in DMSO (700 mL) under nitrogen atmosphere. The mixture was heated to 55° C. during 24 hours. Subsequently, water (70 mL) was added, the reaction mixture was cooled to 2° C. and left at this temperature for 5 hours. The solution was filtered, washed with acetonitrile and dried under vacuum to obtain 30.3 g after assay (68% yield) of gatifloxacin.

EXAMPLE 9

Forty grams of 1-cyclopropyl-6,7-difluoro-1,4-dihydro-8-methoxy-4-oxo-3-quinoline carboxylic acid and 28.4 g (2.1 eq) of 2-methyl piperazine were suspended in DMSO (800 mL) under nitrogen atmosphere. The mixture was heated to 55° C. during 24 hours. Then water (70 mL) was added, the reaction mixture was cooled to 2° C. and left at this temperature overnight. The solution was filtered, washed with acetonitrile and dried under vacuum to obtain 38.5 g after assay (75.8% yield) of gatifloxacin.

EXAMPLE 10

A 100 L reactor was charged with DMSO (120 L) and 2-methylpiperazine (8.6 Kg) at 55° C. under nitrogen atmosphere. 1-cyclopropyl-6,7-difluoro-1,4 dihydro-8-methoxy-4-oxo-3-quinoline carboxylic acid (12 kg, divided in 4 portions of 3 kg each) of were added every 2 hours. After completion of the reaction (about 24 hours, monitoring by HPLC), the reaction mixture was cooled to about 47-50° C. and 24 L of water were added at this temperature. The resulting reaction mixture was cooled to 5° C. over 2 hours and maintained at this holding temperature for a holding time 18 hours. The resulting precipitate was collected by filtration to obtain 15.9 Kg of wet Gatifloxacin (11.6 Kg dry, 76% yield).

EXAMPLE 11

Thirty (30) grams of wet material obtained in example 1 were charged to a 250 mL reactor at ambient temperature, together with 150 mL of water. The slurry (suspension) was stirred at this slurry temperature for a slurry time of 1 hour and the solid was collected by filtration and washed with water (60 mL).

EXAMPLE 12 a: Eighty (80) grams of the wet material obtained in example 1 were charged in a 500 mL reactor at ambient temperature with 400 mL of water. The suspension was stirred at this temperature for 1 hour and the solid was collected by filtration and washed with water (40 mL) to obtain sample 12a.

b: This wet material (13a) was again slurried in water (500 mL) at ambient temperature for 1 hour. The solid was collected by filtration and washed with water (40 mL) and acetonitrile (40 mL) to obtain sample 12b.

EXAMPLE 13

Fifteen grams (15 g) of the wet material obtained in example 1 were charged to a 250 mL flask at ambient temperature with 75 mL of water. The slurry (suspension) was stirred at this slurry temperature for a slurry time of 1 hour, then 30 mL of the acetonitrile was added to the mixture. The suspension was stirred at this temperature for an additional hour. The solid was collected by filtration and washed with acetonitrile (20 mL).

EXAMPLE 14

Thirty grams (30 g) of the wet material obtained in example 1 were charged in a 250 mL reactor at ambient temperature together with 150 mL of a mixture $H_2O$:ACN 70:30. The slurry (suspension) was stirred at this slurry temperature for a slurry time 1 hour and the solid was collected by filtration and washed with the same mixture $H_2O$:ACN (50 mL).

EXAMPLE 15

Fifteen grams (15 g) of the wet material obtained in example 1 were charged to a 250 mL flask at ambient temperature together with 75 mL of water. The slurry (suspension) was stirred at this slurry temperature for a slurry time of 10 minutes, whereafter an aqueous solution of HCl 1% (4 mL) was added dropwise to adjust the pH to pH=6.7. After addition of the HCl solution the suspension was stirred for 1 hour at ambient temperature. The solid was collected by filtration and washed with water (20 mL).

The level of several impurities in the gatifloxacin prepared in the foregoing examples is given in Table I below.

| Experiment | Conditions | Impurity profile | | | | |
| --- | --- | --- | --- | --- | --- | --- |
| | | DesMe GTF | OH- GTF | DiMe GTF | Anti GTF | 2-Me GTF |
| Example 10. | Chemical reaction | 0.08 | 0.24 | ND | 0.02 | 0.19 |
| Example 11. | Slurry in water, RT, 1 hr | 0.07 | ND | ND | ND | 0.06 |
| Example 12a. | Slurry in $H_2O$ 1 hr, RT | 0.07 | ND | ND | ND | 0.06 |
| Example 12b. | $2^{nd}$ slurry in $H_2O$ 1 hr, RT | 0.07 | ND | ND | ND | 0.03 |
| Example 13. | Slurry in water, RT, 1 hr Addition of ACN, 1 hr | 0.07 | ND | ND | ND | 0.04 |
| Example 14. | Slurry in $H_2O$:ACN 7:3 1 hr, RT | 0.07 | ND | ND | ND | 0.04 |
| Example 15. | Slurry in water, RT, 1 hr Adjustment pH 6.7 | 0.07 | ND | ND | ND | 0.04 |

ND = not detected by HPLC method described above

We claim:

1. A method for making Gatifloxacin containing not more than about 0.1 area-% impurities comprising the steps of:
   (a) heating a reaction mixture comprising 2-methylpiperazine and 1-cyclopropyl-6,7-difluoro-1,4-dihydro-8-methoxy-4-oxo-3-quinoline carboxylic acid in a dipolar aprotic solvent to a reaction temperature from about 40°C. to about 70°C. for a reaction time in an atmosphere of inert gas;
   (b) maintaining the reaction mixture at a holding temperature of about 40° C. or less for a holding time, to form a slurry, wherein the holding time is sufficiently long so that there is no further increase in the percent suspended solids for a period of about one-half hour;
   (c) isolating gatifloxacin from the slurry formed in step (b);
   (d) slurrying the isolated gatifloxacin with water or a mixture of water and acetonitrile to form a water slurry; and
   (e) isolating gatifloxacin having about 0.07 area-% or less desmethyl gatifloxacin and about 0.06 area-% or less 2'-methyl gatifloxacin from the water slurry.

2. The method of claim 1 wherein the reaction mixture is formed by portionwise addition of the 1-cyclopropyl-6,7-difluoro-1,4-dihydro-8-meth-oxy-4-oxo-3-quinoline carboxylic acid to a mixture of dipolar aprotic solvent and 2-methylpiperazine.

3. The method of claim 1 further comprising the step of, prior to the maintaining step, concentrating the reaction mixture to a volume that is from about 40% to about 60% of its initial volume by distilling-off dipolar aprotic solvent.

4. A pharmaceutical composition comprising gatifloxacin that contains about 0.07% or less desmethyl gatifloxacin and about 0.06% or less 2'-methytl gatifloxacin.

5. The method according to claim 1, wherein the reaction temperature in step (a) is from about 53° C. to about 57° C.

6. The method according to claim 1, wherein the dipolar aprotic solvent is selected from the group consisting of N,N-dimethylformamide, N,N-dimethylacetamide, dimethylsulfoxide, N-methylpyrolidone, and mixtures thereof.

7. The method according to claim 6, wherein the dipolar aprotic solvent is dimethylsulfoxide.

8. The method according to claim 1, wherein the inert gas is selected from the group consisting of nitrogen and argon.

9. The process according to claim 1, wherein the holding time in step (b) is from about 12 hours to about 24 hours.

10. The method according to claim 1, wherein the holding temperature in step (b) is less than about 25° C.

11. The method according to claim 1, wherein the holding temperature in step (b) is less than about 5° C.

12. The process according to claim 1, wherein the slurrying in step (d) is carried out for a slurry time that is from about thirty minutes to about three hours.

13. The method according to claim 1, wherein slurrying with water or a mixture of water and acetonitrile in step (d) is performed at a temperature of from about 20°C. to about 30° C.

14. Gatifloxacin containing not more than about 0.1 area-% impurities made according to the method of claim 1.

15. The method of claim 11, further comprising prior to or simultaneous with the maintaining step, the step of adding to the reaction mixture co-solvent selected from the group consisting of benzene, toluene, dimethylcarbonate, and water.

* * * * *